United States Patent [19]

Butler et al.

[11] 4,400,570
[45] Aug. 23, 1983

[54] ETHYLBENZENE PRODUCTION EMPLOYING TEA-SILICATE CATALYSTS

[75] Inventors: James R. Butler; Cleve H. Forward; Thomas W. Robison, all of Big Spring, Tex.

[73] Assignee: Cosden Technology, Inc., Dallas, Tex.

[21] Appl. No.: 380,583

[22] Filed: May 21, 1982

[51] Int. Cl.³ .............................................. C07C 2/68
[52] U.S. Cl. ................................................... 585/467
[58] Field of Search ......................................... 585/467

[56] References Cited

U.S. PATENT DOCUMENTS

| | | | |
|---|---|---|---|
| 2,383,179 | 8/1945 | Egloff | 585/467 |
| 3,965,209 | 6/1976 | Butter et al. | 585/467 |
| 4,049,738 | 9/1977 | Young | 585/467 |
| 4,061,724 | 12/1977 | Grose et al. | 423/335 |
| 4,104,319 | 8/1978 | Kaeding | 585/467 |
| 4,283,306 | 8/1981 | Herkes | 252/432 |
| 4,357,323 | 11/1982 | Dwyer et al. | 208/109 |

FOREIGN PATENT DOCUMENTS

| | | | |
|---|---|---|---|
| 21475 | 5/1980 | European Pat. Off. | |
| 507452 | 11/1954 | United Kingdom | 585/468 |
| 2024790 | 1/1980 | United Kingdom | 423/326 |

Primary Examiner—Delbert E. Gantz
Assistant Examiner—Cynthia A. Prezlock
Attorney, Agent, or Firm—Roy W. Hardin

[57] ABSTRACT

A process for producing ethylbenzene by catalytic alkylation employing a TEA-silicate catalyst material and steam co-feed are described. Excellent conversion, selectivity and xylene suppression can be obtained under vapor phase alkylation conditions during production of ethylbenzene using TEA-silicate catalysts and steam co-feed.

10 Claims, No Drawings

ETHYLBENZENE PRODUCTION EMPLOYING TEA-SILICATE CATALYSTS

TECHNICAL FIELD

This invention relates to a process for producing ethylbenzene by contacting suitable reactants under specified conversion conditions in the presence of a TEA-silicate catalyst. In another aspect, this invention relates to ethylbenzene production employing an effective amount of steam co-feed in an ethylbenzene process catalyzed with TEA silicate catalyst materials. A further aspect of this invention relates to a method for producing ethylbenzene in which the amount of unwanted by-products, especially xylene, is suppressed while acceptable conversion and selectivity to desired ethylbenzene product is maintained through the use of steam co-feed and TEA-silicate catalyst materials.

BACKGROUND ART

Ethylbenzene is used predominantly for the production of styrene monomer obtained through dehydrogenation. Presently much of the ethylbenzene being produced is obtained by alkylation of benzene with ethylene under a variety of alkylation conditions. One type of alkylation process which is conventional is to employ relatively high pressures and temperatures to obtain vapor phase reaction conditions wherein the ethylene and benzene are converted in the presence of catalyst materials. Both single and multiple catalyst bed processes are well known in the art. One problem in the production of ethylbenzene by such mwethods is the production of unwanted by-products which can be very detrimental because some of the by-products may be very difficult, or impossible, to separate from the desired ethylbenzene product. Thus, as an example, the production of xylene in these types of processes is very undesirable since separation of xylene from the ethylbenzene product is very difficult from a processing standpoint. In addition to the requirement that the catalyst employed in such processes be selective to the desired ethylbenzene product it is also desirable to obtain acceptable conversion of the reactants to alkylated products. The ability of different catalyst materials to convert the raw feed materials into products is sometimes referred to as its "activity". Conversion is normally measured as a percentage of the amount of feed materials which will be converted into products during the reaction. The ability of the catalyst to maintain high conversion rates (i.e. retain activity) is also important.

Deactivation of catalysts is one major problem in catalytic alkylation processes, since even if high conversion rates are obtained initially, the failure to maintain good conversion over a long period of time requires expensive catalyst changeouts and/or regeneration procedures. As used herein, the term "stability" refers to the relative activity of the catalyst material as a function of time under the conditions of the stated process.

The use of zeolite type catalysts, of both natural and man-made varieties, in hydrocarbon conversion processing has been known for some time. Aluminosilicate type zeolite catalysts, including those known as ZSM-5 and ZSM-12, for example, have been reported to be suitable for hydrocarbon conversion processes and, in particular, for alkylation of aromatic substrates. One problem with these types of catalysts, however, is that they are subject to rapid deactivation in the presence of even small amounts of water. For example, U.S. Pat. No. 4,197,214 describes a special method for stabilizing these types of crystalline zeolites which is indicated to be necessary if rapid deactivation in the presence of reducing atmospheres (such as those found in alkylation reactors) and high temperatures in the presence of steam is to be avoided.

A distinct type of catalyst material which is synthesized from reaction systems essentially free of aluminum containing reagents and which are therefore either entirely free of framework $AlO_4^-$ tetrahedra or contain no crystalographically significant amounts thereof called "TEA-silicates" are disclosed in U.S. Pat. No. 4,104,294. These TEA-silicate catalysts are reportedly capable of adsorbing at least 28% neopentane which has a kinetic diameter of 6.2 angstroms.

Thus it would be desirable to obtain a process in which conversion of reactants to ethylbenzene can be obtained without production of unwanted xylene by-products and without the necessity of regenerating or replacing the catalytic material employed.

SUMMARY OF THE INVENTION

It has now been discovered that alkylation of benzene with ethylene under vapor phase reaction conditions can be effected in a process having high conversion rates and low rates of deactivation with excellent selectivity to ethylbenzene and a reduced amount of xylene formation by employing a TEA-silicate type catalyst material in a process which includes steam co-feed. More specifically, it has been discovered that by introducing benzene and ethylene reactants into a reaction zone maintained at reaction conditions and comprising a TEA-silicate catalyst material and co-feeding steam with the reactants in an amount from about 20,000 to about 100,000 ppm based on the amount of benzene, and allowing alkylation to proceed, excellent conversion to ethylbenzene is achieved and a substantially reduced amount of xylene is obtained.

Thus, in general, the present invention provides a method for producing ethylbenzene by reacting benzene and an ethylating agent in the presence of a TEA-silicate catalyst under conversion conditions which includes steam co-feed. Generally, temperatures in the range of from about 370° C. to about 470° C. are employed with benzene to ethylene molar ratios in the range of from about 2:1 to about 20:1; pressures in the range of from about atmospheric to about 25 atmospheres; and benzene WHSV's in the range of from about 40 to about 200. The particular TEA-silicate material which has been discovered to achieve xylene suppression is a material which is reportedly made in accordance with the disclosures of U.S. Pat. No. 4,104,294 using a solid amorphous silica as the silica source. The silica source employed for the TEA-silicate material specified in the examples hereinbelow contained approximately 0.45% by weight alumina as an impurity. Consequently, the TEA-silicate product contained a relatively high extraneous aluminum content of 0.45% but is clearly nonzeolite in that the crystalographic structure thereof does not contain significant amounts of aluminum.

DETAILED DESCRIPTION

The process of the subject invention generally comprises the steps of feeding ethylene, benzene and water, normally in the form of steam co-feed, to an alkylation reaction zone where the reactants are brought into contact with a TEA-silicate catalyst material under alkylation conditions. The catalyst material is fairly steam stable and is highly selective to the production of ethylbenzene and diethylbenzene in a temperature range of from about 370° C. to about 470° C. Conversion of reactants, as measured by the amount of ethylene actually reacted compared to the amount delivered to the reactor, is high and remains so over commercially acceptable periods of time. Importantly, xylene production can be suppressed dramatically and in some instances to less than 100 ppm of the effluent from the reactor.

The process can be carried out using a variety of process equipment, including a reactor vessel which defines an alkylation zone and contains the TEA-silicate catalyst material. Either single or multiple catalyst beds can be employed in the reaction zone. The benzene and ethylene reactants can be admixed and preheated prior to introduction into the reaction zone where they contact the catalyst beds under reaction conditions further specified hereinbelow. If desied, steam employed in the process can be admixed with the reactants prior to introduction to the reaction zone. After a controlled residence time within the reaction zone, the converted hydrocarbon charge passes out of the reactor where the ethylbenzene products are collected by cooling and other standard recovery techniques. The excess benzene exiting from the reactor is normally recycled in a conventional manner.

The catalyst materials employed in the process of the subject invention can be characterized as crystalline microporous organosilicates which are prepared hydrothermally using a reaction mixture comprising tetraethylammonium cations, alkali metal cations, water and a reactive source of silica. Unlike crystalline zeolite materials which are aluminosilicates comprising three dimensional networks of $SiO_4$ and $AlO_4$ tetrahedra joined by the sharing of oxygen atoms, the crystalline organosilicates employed in the process of the present invention are synthesized from reaction systems which are essentially free of aluminum containing reagents. These TEA-silicate materials can be prepared in accordance with the disclosures of U.S. Pat. No. 4,104,294 which is hereby incorporated by reference. The aluminum content of these materials may vary depending on the amount of aluminum contained in the preparation materials as an impurity. For example, the particular TEA-silicate catalyst materials employed in the process of the subject invention can have a slightly higher aluminum content than that which is disclosed in U.S. Pat. No. 4,104,294 due to aluminum impurities in the solid amorphous silica used in their preparation. These catalysts are hydrophobic and organophilic materials which will adsorb neopentane, suggesting a pore size opening of greater than about 6.2 Angstroms. It is noted that the "TEA-silicates" only contain the organic group in their "as synthesized" form, the organic portions being removed by calcination prior to use as hydrocarbon conversion catalysts.

In general, alkylation zone reaction conditions for the process of the subject invention will include temperatures in the range of from about 300° C. to about 600° C. and preferably in the range of from about 370° C. to about 470° C. Steam co-feed is employed in an amount of from about 20,000 to about 60,000 ppm based on the weight of benzene in the process. Excessive amounts of steam such as, for example, 100,000 ppm have been observed to adversely affect catalytic activity, resulting in a decrease in conversion. An excess of benzene to ethylene is normally employed and in general is in the range of from about 2:1 to about 20:1 molar ratio of benzene:ethylene. Since lower benzene:ethylene ratios result in a higher percentage of ethylbenzene, lower molar ratios within this range are preferred. Weight hourly space velocities (WHSV's) of benzene employed in the process of the subject invention can be in the range of from about 40 to about 200 with WHSV's in the range of from about 80 to about 150 being preferred. Operating pressures between about atmospheric and 25 atmospheres can be used with a range of from about 10 to about 15 atmospheres being preferred.

In an especially preferred process, a TEA-silicate catalyst prepared in accordance with the disclosures of U.S. Pat. No. 4,104,294 but employing a solid amorphous silica containing approximately 0.45 weight percent alumina as impurity is employed. This catalyst material is in the form of 1/16 inch catalyst extrudates and contained 85% of the TEA-silicate catalyst material and 15 weight percent alumina binder. Its average particle size is approximately 3.7 microns. This catalyst material, when employed to produce ethylbenzene from benzene and ethylene, under reaction conditions including temperatures of from 370° C. to 470° C., steam co-feed in an amount of about 40,000 ppm based on benzene, benzene WHSV's of approximately 110 and pressures of about 10 atmospheres with benzene:ethylene molar ratios of approximately 7:1, demonstrated excellent selectivity to ethylbenzene with consistently low production of xylenes. Other organic heavies were also surprisingly low for a catalyst of this large pore size.

The process of the subject invention can be further exemplified through a study of the following example which is not intended to limit the invention in any manner.

EXAMPLE

Benzene and ethylene are introduced into a reaction zone containing a bed of TEA-silicate catalyst material having a particle size of between about 12 and 20 mesh and a bed depth of approximately 8.25 cm. The benzene to ethylene molar feed ratio is held constant at approximately 7:1. The benzene WHSV is held at approximately 110 and pressure is maintained at approximately 10 atmospheres. The product stream from the alkylation reaction zone is analyzed by gas chromatography. The catalyst activity is determined during the trial according to the following formula:

$$\% \text{ Conversion} = \frac{\text{Moles of Ethylbenzene plus 2} \times \text{moles of Diethylbenzene}}{\text{Moles of Ethylene Fed to Reactor}} \times 100\%.$$

The selectivity is determined according to the following formula :

$$\text{Selectivity} = \frac{\text{Weight Ethylbenzene and Diethylbenzene}}{\text{Total Product Weight} \times 100\%} \times 100\%.$$

During a catalyst run of approximately 213.5 hours, the inlet reaction temperature is adjusted from approximately 400° C. to 425° C., and then to 450° C. and 470° C. Steam co-feed in an amount of 40,000 ppm relative to benzene is employed at each temperature and, in addition, 100,000 ppm of steam relative to benzene is employed for a period of time at an inlet reaction temperature of about 450° C. The results of the run are set forth below in Table 1:

TABLE 1

| Run Segment | Catalyst Age, hr. | Temperatures °C. | Steam ppm | Conv. % | Sel. % | Xylene ppm |
|---|---|---|---|---|---|---|
| A | 0–68.5 | 402 | 40,000 | 99.0–83.6 | 94.0–99 | 99 ± 234 |
| B | 68.5–164.5 | 424 | 40,000 | 91.0–84.1 | 98.8–99.3 | 29 ± 27 |
| C | 164.5–188.5 | 446 | 100,000 | 80.9–80.3 | 98.8–99.1 | 47 ± 8 |
| D | 188.5–195.5 | 449 | 40,000 | 95.0–90.1 | 98.9–99.2 | 89 ± 35 |
| E | 195.5–213.5 | 467 | 40,000 | 90.1–87.6 | 98.6 | 274 ± 104 |

The above data indicates that by using a combination of TEA-silicate catalyst materials and steam co-feed, excellent conversion of benzene and ethylene to ethylbenzene can be accomplished while undesirable xylene production as a by-product can be substantially reduced.

One of ordinary skill in the art upon reading the specification and example will appreciate that the process of the subject invention can be modified or adapted in a variety of ways. All such modifications or adaptations which fall within the scope of the appended claims are intended to be covered thereby.

We claim:

1. A process for producing ethylbenzene comprising contacting benzene and ethylene under alkylation conditions which include an effective amount of steam, in the presence of a TEA-silicate catalyst material, the presence of said steam effecting increased catalytic conversion to ethylbenzene.

2. The process of claim 1 wherein steam is present in an amount from about 20,000 to about 60,000 ppm based on benzene.

3. The process of claim 2 wherein said alkylation reaction conditions include temperatures in the range of from about 370° to about 470° C.

4. The process of claim 3 wherein said alkylation reaction conditions comprise pressures in the range of from about atmospheric to about 25 atmospheres.

5. The process of claim 4 wherein said alkylation reaction conditions include benzene WHSV's in the range of from about 40 to about 200.

6. A catalytic vapor phase alkylation process for producing ethylbenzene comprising:
   (a) introducing benzene and ethylene reactants into a reaction zone maintained at alkylation conditions and comprising a TEA-silicate catalyst material;
   (b) co-feeding steam with said reactants in an amount of from about 20,000 to about 60,000 ppm based on the amount of benzene, into said reaction zone; and
   (c) withdrawing from said reaction zone ethylbenzene product.

7. The process of claim 6 wherein said alkylation conditions include temperatures in the range of from about 370° to about 470° C.

8. The process of claim 6 comprising a benzene:ethylene molar ratio in the range of from about 3:1 to about 20:1.

9. The process of claim 6 comprising benzene WHSV's in the range of from about 4 to about 200.

10. A method for reducing xylene by-product production during catalytic alkylation of benzene to ethylbenzene comprising:
    co-feeding an effective amount of steam under alkylation reaction conditions, the presence of said steam reducing the amount of xylene by-product production, and
    employing a TEA-silicate catalyst material.

* * * * *